(12) United States Patent
Davis

(10) Patent No.: US 7,456,322 B2
(45) Date of Patent: Nov. 25, 2008

(54) PROCESS FOR PREPARING 1,3-DIBROMOACETONE, 1-3-DICHLOROACETONE AND EPICHLOROHYDRIN

(75) Inventor: Clark S. Davis, Oakley, CA (US)

(73) Assignee: Dow Global Technologies Inc., Midland, MI (US)

(*) Notice: Subject to any disclaimer, the term of this patent is extended or adjusted under 35 U.S.C. 154(b) by 255 days.

(21) Appl. No.: 10/593,397

(22) PCT Filed: May 17, 2005

(86) PCT No.: PCT/US2005/017193

§ 371 (c)(1), (2), (4) Date: Oct. 4, 2006

(87) PCT Pub. No.: WO2005/115954

PCT Pub. Date: Dec. 8, 2005

(65) Prior Publication Data

US 2008/0249324 A1    Oct. 9, 2008

(51) Int. Cl.
C07C 45/00    (2006.01)
C07D 301/02    (2006.01)

(52) U.S. Cl. .................. 568/388; 568/393; 568/411; 549/518

(58) Field of Classification Search .......... 568/388, 568/393, 411; 549/518
See application file for complete search history.

(56) References Cited

U.S. PATENT DOCUMENTS 4,024,193 A    5/1977    Kruse
4,251,467 A    2/1981    Kurkov
5,997,716 A    12/1999    Roberts et al.

FOREIGN PATENT DOCUMENTS

| JP | 63017874 | 1/1988 |
|----|----------|--------|
| JP | 9104648 | 10/1995 |
| JP | 63-297333 | 12/1998 |
| PL | 176853 | 6/1994 |
| RO | 108962 | 10/1994 |
| SU | 1567568 | 5/1990 |
| WO | WO 03064357 | 8/2003 |

OTHER PUBLICATIONS

Rodygin et al. Selective Monobromination of Ketones by Bis(Dimethylacetamide) Hydrogen Tribomide. Russian Journal of Organic Chemistry, 1994, vol. 30 (6), pp. 881-887.*
Schubert, et al, Chemtech, Apr. 1993, pp. 37-41.

* cited by examiner

Primary Examiner—Sikarl A Witherspoon

(57) ABSTRACT

A process for preparing 1,3-dibromoacetone, 1-3-dichloroacetone and epichlorohydrin which comprises: (a) re-acting acetone with 2 moles of bromine to make a mixture of brominated acetone derivatives and byproduct hydrogen bromide; (b) equilibrating the mixture of brominated acetone derivatives and hydrogen bromide to produce 1,3-dibromoacetone as the major product; (c) crystallizing the 1,3-dibromoacetone; and (d) isolating the 1,3-dibromoacetone. The process may further include the steps of (e) reacting the 1,3-dibromoacetone with a chloride source to produce 1,3-dichloroacetone; (f) hydrogenating the isolated 1,3-dichloroacetone to produce 1,3-dichlorohydrin; and (g) cyclizing the 1,3-dichlorohydrin with a base to produce epichlorohydrin.

39 Claims, No Drawings

PROCESS FOR PREPARING 1,3-DIBROMOACETONE, 1-3-DICHLOROACETONE AND EPICHLOROHYDRIN

The present invention relates to a process for making 1,3-dibromoacetone and 1,3-dichloroacetone. 1,3-dichloroacetone prepared by the process of the present invention is useful for manufacturing epichlorohydrin.

1,3-Dibromoacetone belongs to the class of 1,3-dihaloacetones which includes dichloroacetone and difluoroacetone. These dihaloacetone derivatives have been shown to be useful for making intermediates for pharmaceuticals and fine chemicals as well as industrial chemicals including epichlorohydrin. However, there is currently a need for the preparation of 1,3-dihaloacetone derivatives in high yield.

The preparation of 1,3-dichloroacetone directly from the reaction of acetone with chlorine produces excessive amounts of 1 μl-dichloroacetone as well as trichloroacetone derivatives. It has been proposed that 1,3-dichloroacetone can be made selectively by reaction of acetone with chlorine. For example, Kurkov (U.S. Pat. No. 4,251,467 (Feb. 17, 1981)) discloses making 1,3-dichloroacetone by the reaction of acetone and chlorine in the presence of an iodine containing compound. The costs associated with this process are high due to the high cost of iodine and the production of large amounts of unwanted chlorinated byproducts and hydrogen chloride.

1,3-Dibromoacetone is difficult to prepare in high yield since direct bromination of acetone or bromination of bromoacetone leads to multiple products. An equilibration reaction catalyzed by hydrogen bromide interconverts the products from dibromination of acetone to give a mixture containing monobromoacetone, 1,1-dibromoacetone, 1,3-dibromoacetone and tribromoacetone with varying amounts of higher brominated products and acetone. The equilibrium reaction limits the maximum concentration of 1,3-dibromoacetone to 70 percent of the total mixture.

V. P. Kutrov and A. N. Koskyuk (SU 1,567,568) describe the preparation of 1,3-dibromoacetone by reacting acetone with two molar equivalents of bromine to give a mixture of brominated acetone products. This mixture of brominated acetone products is treated with sodium bisulfite, the sodium bisulfite adduct of 1,3-dibromoacetone is isolated by filtration and then the sodium bisulfite adduct of 1,3-dibromoacetone is decomposed with sulfuric acid. 1,3-Dibromoacetone is isolated from the sulfuric acid solution by filtration and then purified by recrystallization. This process is complex requiring multiple chemical steps, gives 1,3-dibromoacetone in low yield and produces a large amount of brominated acetones derivatives and hydrogen bromide as waste products.

It would be desirable to provide a commercially feasible and effective process for the preparation of 1,3-dibromoacetone and 1,3-dichloroacetone.

In a first aspect, the present invention is a process for preparing 1,3-dibromoacetone which comprises:

(a) reacting acetone with bromine to make a mixture of brominated acetone derivatives and hydrogen bromide byproduct;

(b) equilibrating the mixture of brominated acetone derivatives to produce 1,3-dibromoacetone as the major product;

(c) crystallizing the 1,3-dibromoacetone in the mixture of brominated acetone derivatives; and (d) isolating the 1,3-dibromoacetone from the mixture of brominated acetone derivatives (mother liquor).

In a second aspect, the present invention is a process which comprises.

(a) equilibrating the mixture of brominated acetone derivatives mother liquor remaining from the first aspect with hydrogen bromide to produce 1,3-dibromoacetone as the major product;

(b) crystallizing the 1,3-dibromoacetone in the mixture of brominated acetone derivatives mother liquor; and (c) isolating the 1,3-dibromoacetone from the mixture of brominated acetone derivatives mother liquor.

In a third aspect, the present invention is a process for preparing 1,3-dibromoacetone which comprises:

(a) reacting acetone with bromine to make a mixture of brominated acetone derivatives and hydrogen bromide byproduct;

(b) equilibrating the mixture of brominated acetone derivatives to produce 1,3-dibromoacetone as the major product; and (c) conducting a reactive crystallization of the 1,3-dibromoacetone while concurrently equilibrating the mixture of brominated acetone derivatives.

In a fourth aspect, the present invention is a process which comprises isolating crystalline 1,3-dibromoacetone from the third aspect step (c).

In a fifth aspect, the present invention is a process which comprises:

(a) converting to bromine the hydrogen bromide byproduct produced in the reaction of acetone and bromine; and (b) recycling the recovered bromine for use in the acetone bromination reaction.

In a sixth aspect, the present invention is a process for preparing 1,3-dichloroacetone which comprises:

(a) reacting 1,3-dibromoacetone with a chloride source to produce a mixture of major product 1,3-dichloroacetone and byproduct bromide; and (b) isolating the 1,3-dichloroacetone.

In a seventh aspect, the present invention is a process for preparing epichlorohydrin which comprises:

(a) reacting 1,3-dibromoacetone with a chloride source to produce a mixture of major product 1,3-dichloroacetone and byproduct bromide;

(b) reducing the 1,3-dichloroacetone to produce 1,3-dichlorohydrin; and (c) cyclizing the 1,3-dichlorohydrin with a base to produce epichlorohydrin.

In an eighth aspect, the present invention is a process which comprises:

(a) reacting 1,3-dibromoacetone with a chloride source to produce a mixture of major product 1,3-dichloroacetone and byproduct bromide;

(b) converting the byproduct bromide produced in step (a) to bromine;

(c) recycling the bromine to the acetone-bromination reaction; and (d) optionally, recycling any chloride source formed in step (b) to step (a).

In a ninth aspect, the present invention is a process which comprises preventing or minimizing the formation of large amounts of tetrabromoacetone by thoroughly mixing the bromine and the acetone before the addition of a catalyst or the reaction self-initiates.

In a tenth aspect, the present invention is a process which comprises using a mixture of brominated acetone derivatives as the solvent for the reaction of acetone and bromine.

Other aspects of the present invention will become apparent from the following detailed description and claims.

The bromoacetone derivatives formed by reacting acetone with bromine, that is in the acetone bromination step of the present invention are represented by Formula I as follows:

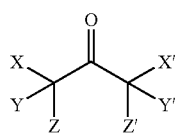

Formula I wherein X is bromine, Z and Z' are hydrogen, Y, Y' and X' are individually hydrogen or bromine.

It has been found that during the reaction of acetone with two moles of bromine that the formation of higher brominated acetone derivatives such as tetrabromoacetone can be reduced by the rapid mixing of bromine and acetone such that the reaction mass is well mixed as the reaction begins. Rapid mixing of acetone and bromine prior to the introduction or spontaneous formation of hydrogen bromide catalyst results in significantly lower tetrabromoacetone concentrations. The acetone and bromine may be premixed before introduction of solvent.

It has also been found that a mixture of brominated acetone derivatives can be used as the solvent for the reaction of acetone with two moles of bromine without formation of undesirable byproducts. The mixture of brominated acetone derivatives can include any composition where bromoacetone, 1,1-dibromoacetone, 1,3-dibromoacetone, and tribromoacetone are the major components.

Those with skill in the art will readily appreciate that the bromination of acetone can be conducted by continuous or batch methods.

A key aspect of the present invention is the discovery that 1,3-dibromoacetone may be isolated from an equilibrated mixture of brominated acetone derivatives resulting from the reaction of acetone with 2 moles of bromine by crystallization and separation of the solid 1,3-dibromoacetone from the remaining brominated acetone derivatives mother liquor. The crystallization and separation of the solid 1,3-dibromoacetone and the brominated acetone derivatives mother liquor may be accomplished by known methods.

The crystallization and isolation of 1,3-dibromoacetone may be conducted either in the presence or absence of a solvent or mixture of solvents. The solvent or mixture of solvents may be selected such that the solvent is inert to the reagents and the 1,3-dibromoacetone and brominated acetone derivatives mother liquor can be isolated from the solvent.

Examples of suitable crystallization solvents include aromatic and aliphatic hydrocarbons, chlorinated hydrocarbons, ethers, esters, alcohols and ketones or mixture thereof. The crystallization may be repeated to increase the purity of the 1,3-dibromoacetone product.

The yield of the acetone bromination process may be increased by equilibration of the remaining brominated acetone derivatives mother liquors in the presence of hydrogen bromide. The mother liquors remaining after removal of crystalline 1,3-dibromoacetone including bromoacetone, 1,1-dibromoacetone and tribromoacetone can be equilibrated to give 1,3-dibromoacetone as the major product. The combination of crystallization and isolation of 1,3-dibromoacetone followed by equilibration of the remaining mother liquors can be repeated until essentially complete conversion to 1,3-dibromoacetone is achieved. This equilibration step may be conducted as a separate step or the mother liquors may be recycled to the acetone bromination reaction step where it could serve as all or part of the reaction solvent. The mother liquors may also be directly added to an equilibration step following the reaction of acetone with bromine.

Surprisingly, it has also been found that cooling a solution of the dibromoacetone mixture in the presence of hydrogen bromide results in reactive crystallization of 1,3-dibromoacetone. Simultaneous crystallization of 1,3-dibromoacetone and equilibration of the remaining mixture of bromoacetone, 1,1-dibromoacetone and tribromoacetone results in conversion of the mixture to 1,3-dibromoacetone in high yield. The concentration of 1,3-dibromoacetone in the overall contents including both crystallized 1,30-dibromoacetone and the equilibrium solution can be increased to greater than 95 percent by reactive crystallization.

The reactive crystallization of 1,3-dibromoacetone can also be conducted by separation of 1,3-dibromoacetone from an equilibrating brominated acetone mixture as the 1,3-dibromoacetone is formed. Removal of crystalline 1,3-dibromoacetone allows conversion of the other materials present in the equilibrium to 1,3-dibromoacetone in high yield.

Those who are skilled in the art will recognize that the crystallization or the reactive crystallization of 1,3-dibromoacetone may be conducted by suspension or solid layer crystallization. Suspended crystals may be separated by filtration. The crystallization and isolation processes may be conducted in batch, semi-batch or continuous systems.

The crystallization temperature is a critical aspect and is dependent upon the starting composition of the 1,3-dibromoacetone mixture and the presence of crystallization solvents but can be generally be carried out at temperatures between −30° C. and the melting point of pure 1,3-dibromoacetone.

The hydrogen bromide concentration in reactive crystallization conditions should be high enough to equilibrate the brominated acetone derivative in a timely fashion. It can be employed in a concentration of from 0.01 percent to 10 percent. However, low catalyst concentrations require longer equilibration times.

The present invention also encompasses the preparation of 1,3-dichloroacetone from 1,3-dibromoacetone by reacting 1,3-dibromoacetone with a chloride source to produce 1-bromo-3-chloroacetone which is further converted to 1,3-dichloroacetone. The chloride source can be, for example, lithium chloride, sodium chloride, potassium chloride, magnesium chloride, calcium chloride, manganese chloride, zinc chloride, hydrochloric acid, ammonium chloride, tetramethylammonium chloride, tetraethylammonium chloride, Dowex Marathon MSA ion exchange Resin and poly(4-vinylpyridine), cross-linked, methyl chloride quaternary salt. Other suitable chloride sources include hydrogen chloride, inorganic ionic chlorides and organic chlorides including amine hydrochloride salts, quaternary ammonium salts and phosphonium chloride salts and combinations thereof.

The chloride source is employed in a chloride source to dibromoacetone mole ratio of from 0.1:1 to 200:1, preferably from 1 to 100 and, most preferably from 2 to 75. The reaction of 1,3-dibromoacetone or the intermediate 1-bromo-3-chloroacetone with a chloride source can be repeated to increase conversion.

The reaction can be carried out in the absence or presence of a solvent. If employed, the solvent can be used in an amount up to 99 percent by weight.

If the solvent is employed, the solvents which can be employed in the present invention include, for example, water, organic solvents such as, for example, alcohols, ethers, esters, ketones, chlorinated hydrocarbons and combinations thereof.

The reaction temperature is not critical provided that the reactants and product are stable to the conditions, but, in general, the reaction temperature is from 0° C. to 200° C., preferably from 10° C. to 175° C. and, most preferably from 20° C. to 150° C.

The reaction pressure is also not critical but, in general, the reaction pressure is from vacuum to 3000 psig.

The reaction can be conducted using continuous, batch, semi-batch and/or fixed bed reactors or combinations thereof.

The product 1,3-dichloroacetone can be recovered from the chloride source that contains the bromide byproduct by known methods such as extraction or distillation.

1,3-dichloroacetone can be purified by known methods such as crystallization or distillation. Unreacted 1,3-dibromoacetone and the 1-bromo-3-chloroacetone intermediate obtained from 1,3-dichloroacetone purification may be recycled to increase conversion.

One feature of the present invention is to convert the byproduct hydrogen bromide from the dibromoacetone forming reaction and the bromide byproduct remaining after the dichloroacetone forming reaction to bromine for recycle. The recovery of bromide byproducts, their conversion to bromine, and the recycle of bromine to bromination reactions may be carried out by methods known in the art. For example, as described in Schubert et al, Chemtech, April 1993, pages 37-41. Hydrogen bromide can be converted to bromine by oxidants such as oxygen, including air, chlorine and hydrogen peroxide. Hydrogen bromide can be converted to an aqueous solution of hydrobromic acid and the hydrobromic acid oxidized to bromine. The hydrogen bromide or hydrobromic acid can be neutralized to form bromides salts. Treatment of bromide salts with chlorine to produce bromine and chloride salts is currently practiced commercially. The chloride salts, hydrochloric acid or hydrogen chloride resulting from the recovery of bromine may be recycled to the reaction of 1,3-dibromoacetone with a chloride source.

Ion exchange resins, for example, may be regenerated with a chloride source to remove the bromide byproduct from the resin and the bromide byproduct converted to bromine for recovery and recycle.

1,3-Dichloroacetone can be converted to 1,3-dichloro-2-propanol by various known processes. Examples of conversion of 1,3-dichloroacetone to 1,3-dichloro-2-propanol include WO 2003064357, U.S. Pat. No. 4,024,193, Japanese Patent No. 9104648 and Japanese Patent No. 63-297333.

Conversion of 1,3-dichloro-2-propanol to epichlorohydrin is well known in the art of manufacturing epichlorohydrin. The reaction is usually conducted by treating a dichloropropanol with a strong base such as an aqueous alkyl metal hydroxide or through electrochemical treatment. Examples of conversion of dichloropropanol to epichlorohydrin using bases are described in Polish Patent No. 176853, Romanian Patent No. 108962 and Japanese Patent No. 63017874. 1,3-dichloro-2-propanol can also be converted to epichlorohydrin using electrochemical treatment as described in U.S. Pat. No. 5,997,716.

The following working examples are given to illustrate the invention and should not be construed as limiting its scope. Unless otherwise indicated, all parts and percentages are by weight and product analysis is by gas chromatography area percent excluding solvent.

EXAMPLE 1

Acetone Bromination in Ethyl Acetate with Rapid Addition of Bromine

A 2000 mL jacketed glass reactor was equipped with a stirrer and a magnetic stir bar, addition funnel and a cold finger condenser charged with ice and vented to a pair of gas scrubbers charged with water. The reactor was charged with 136.6 grams of ethyl acetate and 19.5 grams of acetone and the solution was warmed to 30° C. 107.4 grams of bromine was charged to the addition funnel and then added to the reactor over 5 seconds with rapid mixing. The reaction self initiated and was complete within 45 seconds as evidenced by the disappearance of the bromine color. The reaction mixture was sparged with nitrogen for 30 minutes. Analysis of the reaction products was: 13.0 percent bromoacetone, 5.4 percent 1,1-dibromoacetone, 70.5 percent 1,3-dibromoacetone, 11.1 percent tribromoacetone. Tetrabromoacetone was present at less than 0.2 percent.

COMPARATIVE EXAMPLE A

Acetone Bromination in Ethyl Acetate with Bromine Addition Over 15 Minutes as Described in SU 1,567,568

A 2000 mL jacketed glass reactor was equipped with a stirrer and a magnetic stir bar, addition funnel and a cold finger condenser charged with ice and vented to a pair of gas scrubbers charged with water. The reactor was charged with 136.2 grams of ethyl acetate and 31.3 grams of acetone and the solution warmed to 30° C. 170.0 grams of bromine was charged to the addition funnel and added to the acetone solution over 15 minutes with rapid mixing. The reaction mixture was sparged with nitrogen for 30 minutes. Analysis of the reaction products was 12.9 percent bromoacetone, 8.3 percent 1,1-dibromoacetone, 62.3 percent 1,3-dibromoacetone, 15.6 percent tribromoacetone and 2.4 percent tetrabromoacetone.

EXAMPLE 2

Acetone Bromination in Brominated Acetone Mixture

A 2000 mL jacketed glass reactor was equipped with a stirrer and a magnetic stir bar, addition funnel, dip tube for gas addition and a cold finger condenser charged with dry ice/acetone and vented to a pair of gas scrubbers charged with water. The reactor was charged with 150.1 grams of a brominated acetone mixture consisting of 9.5 percent bromoacetone, 4.7 percent 1,1-dibromoacetone, 71.7 percent 1,3-dibromoacetone, 13.8 percent tribromoacetone and 0.4 percent tetrabromoacetone. 16.1 Grams of acetone was added to the brominated acetone mixture and the solution was stirred at 20° C. 88.7 grams of bromine was added to the addition funnel and then charged to the reactor within 5 seconds and the solution was stirred for 1 minute. A catalytic amount of hydrogen bromide was added to the reaction mixture to initiate the reaction. The reaction was complete within 60 seconds as evidenced by the cessation of gas evolution. The reaction mixture was stirred for 90 minutes. Analysis of the reaction products was: 0.5 percent acetone, 10.0 percent bromoacetone, 5.0 percent 1,1-dibromoacetone, 69.2 percent 1,3-dibromoacetone, 14.9 percent tribromoacetone and 0.4 percent tetrabromoacetone. The reaction mixture was discharged into 100 grams of water and the layers separated giving 207 grams of dibromoacetone mixture.

EXAMPLE 3

Reactive Crystallization of Dibromoacetone Mixture 1,3-Dibromoacetone product mixture prepared according to Example 1 was washed with water and the solvent removed under vacuum. Hydrogen bromide, 0.5 grams, was added to 50.2 grams of the bromination product mixture. The solution was cooled to 10° C. and seeded with 1,3-dibromoacetone crystals. The suspension was held at 9-10° C. until it was a solid mass. Analysis of the resulting material was 0.4 percent bromoacetone, 0.3 percent 1,1-dibromoacetone, 97.3 percent 1,3-dibromoacetone and 2.1 percent tribromoacetone.

EXAMPLE 4

Reactive Crystallization of Dibromoacetone Mixture with Filtration of 1,3-Dibromoacetone A 2000 mL jacketed glass reactor was equipped with a stirrer and a magnetic stir bar, thermometer and a dip tube for gas addition was used a crystallization vessel. Another dip tube for slurry transfer was connected to a 1000 mL jacketed glass sintered glass pressure filter by means of tubing containing a ball valve. The bottom of the pressure filter was connected by means of tubing containing a ball valve to the crystallizer to allow liquid return. The pressure filter was equipped with a vent valve and a nitrogen inlet valve. The crystallizer was charged with 2011 grams of dibromoacetone mixture consisting of 13.0 percent bromoacetone, 5.3 percent 1,1-dibromoacetone, 67.2 percent 1,3-dibromoacetone and 11.0 percent tribromoacetone as analyzed by gas chromatography area percent. 17.0 grams of hydrogen bromide was added and the solution was cooled to 11.5° C. The equilibrated mixture was seeded with 7.0 grams of 1,3-dibromoacetone. 1,3-Dibromoacetone crystals were isolated periodically by charging the slurry of 1,3-dibromoacetone crystals in the crude dibromoacetone mixture to the pressure filter and removing the mother liquor by pressuring the filter and venting the liquid back into the crystallizer. After 24 hours, a total of 906 grams of 1,3-dibromoacetone crystals had been collected. Analysis of the remaining 1108 grams of mother liquor by was 12.8 percent bromoacetone, 5.0 percent 1,1-dibromoacetone, 67.0 percent 1,3-dibromoacetone and 10.5 percent tribromoacetone.

EXAMPLE 5

1,3-Dibromoacetone Preparation, Isolation by Solvent Crystallization, Byproduct Equilibration and 1,3-Dibromoacetone Isolation A 2000 mL jacketed glass reactor was equipped with a stirrer and a magnetic stir bar, addition funnel, dip tube for gas addition and a cold finger condenser charged with ice and vented to a pair of gas scrubbers charge with water was charged with 150 grams of ethyl acetate and 16.5 grams of acetone and the solution was cooled to 10° C. 91.6 grams of bromine was charged to the addition funnel, was then added to the acetone solution over 5 seconds. The solution was stirred 5 minutes before addition of a catalytic amount of hydrogen bromide. The reaction mixture was sparged with nitrogen for 30 minutes after the disappearance of the bromine color. Solvent was removed under vacuum and the brominated acetone mixture was mixed with 178 grams of 21 percent diethyl ether/79 percent pentane and cooled to 5° C. at which point crystals formed. The suspension was cooled to 0° C. and held for 1 hour. The crystals were isolated, washed with 21 percent ether/79 percent pentane and dried to give 31.4 grams. Analysis of the crystalline product was: 0.1 percent bromoacetone, 99.1 percent 1,3-dibromoacetone and 0.7 percent tribromoacetone. The mother liquor from the crystallization was combined with the washes and the solvent removed under vacuum. 30 grams of 12 percent hydrogen bromide in ethyl acetate was added to the concentrated mother liquor and stirred at room temperature for 95 minutes. The equilibrated solution was washed with water and the solvent removed under vacuum. 98 Grams of 21 percent ether/79 percent pentane was added to the equilibrated mother liquor and the resulting solution was cooled until it became cloudy at which point it was seeded with 1,3-dibromoacetone crystals. The suspension was cooled to 0° C. over an hour. The crystals were isolated, washed with 21 percent ether/79 percent pentane and dried to give 11.9 grams. Analysis of the crystalline product was: 98.3 percent 1,3-dibromoacetone. Concentration of the mother liquor and the washes under vacuum gave 14.6 grams of brominated acetone derivatives.

EXAMPLES 6-17

General Procedure for Dichloroacetone Preparation

Mix 1,3-dibromoacetone with a chloride source in a 6.0 mL serum bottle. Place the solution in a 60° C. to 80° C. water bath and stir for 5 to 60 minutes. Cool the solution to room temperature, extract the brominated acetone derivatives with 10 milliliters of diethyl ether and analyze the ether layer by gas chromatography. The results are shown in Table 1. Also shown in Table 1 are the chloride sources used, the amounts of chloride source and products 1,3-dichloroacetone (1,3-DCA), 1-bromo-3-chloroacetone (1-Br-3—ClA) and 1,3-dibromoacetone (1,3-DBA).

TABLE 1

| Example | CHLORIDE SOURCE | Amount (g) | 1,3-dibromo acetone (g) | BROMINATED ACETONE DERIVATIVES YIELD (percent) | | |
|---|---|---|---|---|---|---|
| | | | | 1,3-DBA | 1,3-DCA | 1-Br-3-ClA |
| 6 | Potassium chloride | 13.8 | 2.0 | 0 | 95.3 | 4.6 |
| 7 | Magnesium chloride hexahydrate | 28.3 | 1.5 | 0.1 | 94.5 | 5.4 |
| 8 | Lithium chloride | 7.9 | 2.0 | 2.1 | 74.4 | 23.5 |
| 9 | Calcium chloride dihydrate | 27.2 | 2.0 | 0.3 | 91.1 | 8.6 |
| 10 | Zinc chloride | 25.3 | 2.0 | 78.0 | 2.5 | 19.5 |
| 11 | Sodium chloride | 10.8 | 2.0 | 0.1 | 95.1 | 4.8 |
| 12 | Ammonium chloride | 9.9 | 2.0 | 0.1 | 94.7 | 5.2 |
| 13 | Tetramethyl ammonium chloride | 20.3 | 2.0 | 0 | 99.0 | 1.0 |
| 14 | Hydrochloric acid | 18.3 of 37 percent conc. | 2.0 | 3.1 | 71.0 | 25.9 |
| 15 | Manganese dichloride tetrahydrate | 20.0 | 1.0 | 0.2 | 93.0 | 6.8 |

TABLE 1-continued

| Example | CHLORIDE SOURCE | Amount (g) | 1,3-dibromo acetone (g) | BROMINATED ACETONE DERIVATIVES YIELD (percent) | | |
|---|---|---|---|---|---|---|
| | | | | 1,3-DBA | 1,3-DCA | 1-Br-3-ClA |
| 16 | Poly(4-vinylpyridine) methyl chloride | 10.0 | 0.4 | 0 | 97.4 | 2.6 |
| 17 | Dowex Marathon MSA | 10.0 | 10 | 0 | 96.8 | 3.2 |

The following Examples 18-21 demonstrate the use of different chloride to 1,3-DBA mole ratios in the preparation of 1,3-dichloroacetone from 1,3-dibromoacetone and a chloride source.

EXAMPLE 18

2.0 grams of 1,3-dibromoacetone was mixed with 2.7 grams of sodium chloride (1:5 mole ratio) in 9.6 grams water in a 60 mL serum bottle. The solution was placed in an 80° C. water bath and stirred for 10 minutes. The solution was cooled to room temperature, extracted with 10 mL of diethyl ether and the ether layer analyzed by gas chromatography to give: 26.0 percent 1,3-dibromoacetone, 33.1 percent 1-bromo-3-chloroacetone and 40.9 percent 1,3-dichloroacetone.

EXAMPLE 19

2.0 grams of 1,3-dibromoacetone was mixed with 5.4 grams of sodium chloride (1:10 mole ratio) in 19.2 grams water in a 60 mL serum bottle. The solution was placed in an 80° C. water bath and stirred for 10 minutes. The solution was cooled to room temperature, extracted with 10 mL of diethyl ether and the ether layer analyzed by gas chromatography to give: 4.2 percent 1,3-Dibromoacetone, 19.6 percent 1-bromo-3-chloroacetone and 76.2 percent 1,3-dichloroacetone.

EXAMPLE 20

2.0 grams of 1,3-dibromoacetone was mixed with 8.1 grams of sodium chloride (1:15 mole ratio) in 28.8 grams water in a 60 mL serum bottle. The solution was placed in an 80° C. water bath and stirred for 10 minutes. The solution was cooled to room temperature, extracted with 10 mL of diethyl ether and the ether layer analyzed by gas chromatography to give: 0.3 percent 1,3-dibromoacetone, 8.3 percent 1-bromo-3-chloroacetone and 91.4 percent 1,3-dichloroacetone.

The following Examples 21-23 demonstrate the use of different solvent concentrations in the preparation of 1,3-dichloroacetone from 1,3-dibromoacetone and a chloride source.

EXAMPLE 21

2.0 grams of 1,3-dibromoacetone was mixed with 10.8 grams of sodium chloride in 40 grams water in a 60 mL serum bottle. The solution was placed in an 60° C. water bath and stirred for 5 minutes. The solution was cooled to room temperature, extracted with 10 mL of diethyl ether and the ether layer analyzed by gas chromatography to give: 26.6 percent 1,3-dibromoacetone, 37 percent 1-bromo-3-chloroacetone and 36.4 percent 1,3-dichloroacetone.

EXAMPLE 22

1.0 gram of 1,3-dibromoacetone was mixed with 5.4 grams of sodium chloride in 40 grams water in a 60 mL serum bottle. The solution was placed in a 60° C. water bath and stirred for 5 minutes. The solution was cooled to room temperature, extracted with 10 mL of diethyl ether and the ether layer analyzed by gas chromatography to give: 12.1 percent 1,3-dibromoacetone, 47.0 percent 1-bromo-3-chloroacetone and 40.9 percent 1,3-dichloroacetone.

EXAMPLE 23

0.5 grams of 1,3-dibromoacetone was mixed with 2.7 grams of sodium chloride in 40 grams water in a 60 mL serum bottle. The solution was placed in an 60° C. water bath and stirred for 5 minutes. The solution was cooled to room temperature, extracted with 10 mL of diethyl ether and the ether layer analyzed by gas chromatography to give: 39.6 percent 1,3-dibromoacetone, 48.1 percent 1-bromo-3-chloroacetone and 12.3 percent 1,3-dichloroacetone.

Examples 24-25 demonstrate the preparation of 1,3-dichloroacetone from 1,3-dibromoacetone and a chloride source at ambient temperature.

EXAMPLE 24

4.9 grams of 1,3-dibromoacetone was mixed with 38.4 grams of tetraethylammonium chloride in 10.0 grams water in a 60 mL serum bottle. The solution was stirred for 30 minutes at ambient temperature, extracted with 10 mL of diethyl ether and the ether layer analyzed by gas chromatography to give: 0.1 percent 1,3-Dibromoacetone, 4.3 percent 1-bromo-3-chloroacetone and 95.2 percent 1,3-dichloroacetone.

EXAMPLE 25

2.0 grams of 1,3-dibromoacetone was mixed with 13.8 grams of potassium chloride in 37.4 grams water in a 60 mL serum bottle. The solution was warmed slightly to melt the 1,3-dibromoacetone crystals and then stirred at ambient temperature for 22 hours. The solution was extracted with 10 mL of diethyl ether and the ether layer analyzed by gas chromatography to give: 0.1 percent 1,3-dibromoacetone, 3.7 percent 1-bromo-3-chloroacetone and 96.3 percent 1,3-dichloroacetone.

Examples 26-28 demonstrate the use of organic solvents in the preparation of 1,3-dichloroacetone from 1,3-dibromoacetone and a chloride source.

EXAMPLE 26

0.4 grams of 1,3-dibromoacetone was mixed with 10.0 grams of poly(4-vinylpyridine)methyl chloride quaternary salt in 10.0 grams diethyl ether in a 60 mL serum bottle. The solution was placed in a 60° C. water bath and stirred for 60 minutes. The solution was cooled to room temperature and the ether layer analyzed by gas chromatography to give: 0 percent 1,3-dibromoacetone, 5.7 percent 1-bromo-3-chloroacetone and 94.3 percent 1,3-dichloroacetone.

EXAMPLE 27

0.4 grams of 1,3-dibromoacetone was mixed with 10.0 grams of Dowex Marathon MSA in 10.0 grams diethyl ether in a 60 mL serum bottle. The solution was placed in a 60° C. water and stirred for 60 minutes. The solution was cooled to room temperature and the ether layer analyzed by gas chromatography to give: 0.2 percent 1,3-dibromoacetone, 7.8 percent 1-bromo-3-chloroacetone and 92.0 percent 1,3-dichloroacetone.

EXAMPLE 28

0.29 grams of 1,3-dibromoacetone was mixed with 4.0 grams of calcium chloride dihydrate in 1.0 grams methanol in a 60 mL serum bottle. The solution was placed in a 60° C. water and stirred for 60 minutes. The solution was cooled to room temperature and the ether layer analyzed by gas chromatography to give: 0 percent 1,3-dibromoacetone, 1.7 percent 1-bromo-3-chloroacetone, 89.6 percent 1,3-dichloroacetone and 8.7 percent derivatives from the reaction of methanol with 1,3-dichloroacetone.

EXAMPLE 29

In this example, no solvent was employed.

0.65 grams of 1,3-dibromoacetone was mixed with 10.0 grams of molten tetraethylammonium chloride in a 60 mL serum bottle. The solution was stirred at 60° C. for 5 minutes. A 1 mL sample was added to 1 mL water and extracted with 2 mL diethyl ether and the ether layer analyzed by gas chromatography to give: 0 percent 1,3-dibromoacetone, 1.1 percent 1-bromo-3-chloroacetone and 98.9 percent 1,3-dichloroacetone.

EXAMPLE 30

This example demonstrates multiple reactions employed in the preparation of 1,3-dichloroacetone from 1,3-dibromoacetone and a chloride source.

31.3 grams of 1,3-dibromoacetone was mixed with 217 grams potassium chloride in 557 grams water and the mixture was stirred in a 60° C. bath for 10 minutes. The mixture was cooled to 20° C. and extracted 6 times with 150 grams dichloromethane with recovery of dichloromethane from the dichloroacetone product between extractions by distillation under reduce pressure. The resulting dichloroacetone product was mixed with 218 grams potassium chloride in 563 grams water and the mixture was stirred in a 60° C. bath for 10 minutes. The mixture was cooled to 20° C. and extracted 6 times with 150 grams dichloromethane with recovery of dichloromethane from the dichloroacetone product between extractions by distillation under reduce pressure. A total of 18.0 grams (98 percent yield) of 1,3-dichloroacetone was recovered. Analysis of the crystalline product was >99.5 percent 1,3-dichloroacetone.

What is claimed is:

1. A process for preparing 1,3-dibromoacetone which comprises:
   (a) reacting acetone with bromine to make a mixture of brominated acetone derivatives and byproduct hydrogen bromide;
   (b) equilibrating the mixture of brominated acetone derivatives to produce 1,3-dibromoacetone as the major product;
   (c) crystallizing the 1,3-dibromoacetone in the mixture of brominated acetone derivatives mother liquor; and
   (d) isolating the 1,3-dibromoacetone from the mixture of brominated acetone derivatives.

2. The process of claim 1 wherein steps (c) and (d) are carried out substantially simultaneously.

3. The process of claim 1 which further comprises:
   (e) equilibrating the mixture of brominated acetone derivatives from step (d) to produce 1,3-dibromoacetone as the major product; and
   (f) crystallizing the 1,3-dibromoacetone from the mixture of equilibrated brominated acetone derivatives prepared in step (e)
   (g) isolating the 1,3-dibromoacetone from the mixture of equilibrated brominated acetone derivatives.

4. The process of claim 2 wherein steps (f) and (g) are carried out substantially simultaneously.

5. The process of claim 3 which further comprises repeating in sequential order steps (e), (f) and (g) until essentially complete conversion to 1,3-dibromoacetone is achieved.

6. The process of claim 1 or claim 3 wherein the crystallization step is carried out by suspension or solid layer crystallization.

7. The process of claim 1 or claim 3 where the crystallization is conducted in a solvent or mixture of solvents.

8. The process of claim 7 were the solvent or mixture of solvents is selected from the group consisting essentially of aromatic and aliphatic hydrocarbons, chlorinated hydrocarbons, ethers, esters, alcohols and ketones or mixtures thereof.

9. A process for preparing 1,3-dibromoacetone which comprises:
   (a) reacting acetone with bromine to make a mixture of brominated acetone derivatives and hydrogen bromide byproduct;
   (b) equilibrating the mixture of brominated acetone derivatives to produce 1,3-dibromoacetone as the major product; and
   (c) substantially simultaneously (i) crystallizing the 1,3-dibromoacetone and (ii) equilibrating the mixture of brominated acetone derivatives such that the conversion of 1,3-dibromoacetone increases above its liquid equilibrium concentration in the mixture of brominated acetone derivatives.

10. The process of claim 9 wherein the mixture of 1,3-dibromoacetone and equilibrating brominated acetone derivatives consist of greater than 75 weight percent 1,3-dibromoacetone.

11. The process of claim 9 wherein solid 1,3-dibromoacetone is removed from the equilibrating mixture of brominated acetone derivatives.

12. The process of claim 1 or claim 9 wherein the brominated acetone derivatives include bromoacetone, 1,1-dibromoacetone, 1,3-dibromoacetone, and tribromoacetone.

13. The process of claim 1 or claim 9 wherein the brominated acetone derivatives include acetone, bromoacetone, 1,1-dibromoacetone, 1,3-dibromoacetone, tribromoacetone, and tetrabromoacetone.

14. The process of claim 1 or claim 3 or claim 9 wherein the equilibration step is carried out in the presence of a catalyst.

15. The process of claim 14 wherein the catalyst is hydrogen bromide.

16. The process of claim 1 or claim 9 wherein in step (a) the acetone and bromine are thoroughly mixed at the beginning of the reaction such that the formation of tetrabromoacetone is prevented or substantially minimized.

17. The process of claim 1 or claim 9 wherein step (a) is carried out in the presence of a solvent consisting of a mixture of brominated acetone derivatives.

18. The process of claim 17 wherein the brominated acetone derivatives include bromoacetone, 1,1-dibromoacetone, 1,3-dibromoacetone, and tribromoacetone.

19. The process of claim 17 wherein the brominated acetone derivatives include acetone, bromoacetone, 1,1-dibromoacetone, 1,3-dibromoacetone, tribromoacetone, and tetrabromoacetone.

20. The process of claim 17 wherein the mixture of brominated acetone derivatives includes (i) unequilibrated product from claim 1 or claim 9 step (a); (ii) equilibrated product from claim 1 or claim 9 step (b); a mother liquor from the crystallization of 1,3-dibromoacetone in a mixture of brominated acetone derivatives; and (iv) any combination of (i), (ii) or (iii).

21. The process of claim 1 or claim 9 which further comprises recovering the hydrogen bromide formed as a byproduct in the bromination of acetone and converting the hydrogen bromide to molecular bromine.

22. The process of claim 21 which further comprises recycling the bromine to the acetone bromination reaction.

23. The process of claim 1 wherein any one of steps (a), (b), (c) or (d) is carried out in a continuous manner.

24. The process of claim 9 wherein any one of steps (a), (b) or (c) is carried out in a continuous manner.

25. The process of claim 22 where any step is carried out in a continuous manner.

26. A process for preparing 1,3-dichloroacetone which comprises reacting 1,3-dibromoacetone with a chloride source to produce 1,3-dichloroacetone.

27. The process of claim 26 wherein the chloride source is selected from the group consisting of hydrogen chloride, hydrochloric acid, inorganic ionic chlorides, amine hydrochloride salts, quaternary ammonium salts, phosphonium chloride salts and combinations thereof.

28. The process of claim 26 wherein the reaction product includes a mixture of 1,3-dichloroacetone and byproduct bromide after the reaction step.

29. The process of claim 26 including the step of isolating the 1,3-dichloroacetone.

30. The process of claim 26 wherein the 1,3-dibromoacetone is prepared by the process of claim 1 or claim 9.

31. The process of claim 28 which further comprises converting the byproduct bromide to molecular bromine.

32. The process of claim 28 which further comprises converting the byproduct bromide to molecular bromine and regenerating the chloride source.

33. The process of claim 31 or claim 32 which further comprises recycling the bromine to the acetone bromination reaction.

34. The process of claim 32 which further comprises recycling the chloride source to the reaction of 1,3-dibromoacetone with a chloride source.

35. The process of claim 31 or claim 32 wherein the conversion of byproduct bromide to bromine is conducted using continuous reactors.

36. A process for preparing epichlorohydrin which comprises:
    (a) reacting 1,3-dibromoacetone with a chloride source to produce 1,3-dichloroacetone;
    (b) hydrogenating the 1,3-dichloroacetone prepared in step (a) in the presence of a catalyst to produce 1,3-dichlorohydrin; and
    (c) cyclizing the 1,3-dichlorohydrin with a base to produce epichlorohydrin.

37. The process of claim 36 wherein the 1,3-dibromoacetone is prepared by the process of claim 1 or claim 9.

38. The process of claim 26 or claim 36 wherein the reaction of 1,3-dibromoacetone is conducted using continuous and/or fixed bed reactors.

39. The process of claim 29 or claim 36 wherein the 1,3-dichloroacetone is isolated by continuous distillation or continuous extraction.

* * * * *